US00PP21968P2

(12) United States Plant Patent
Bergman

(10) Patent No.: US PP21,968 P2
(45) Date of Patent: Jun. 7, 2011

(54) ***CHRYSANTHEMUM* PLANT NAMED 'SYNDURANGO DARK'**

(50) Latin Name: *Chrysanthemum×morifolium*
Varietal Denomination: Syndurango Dark

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/802,172

(22) Filed: Jun. 1, 2010

(51) Int. Cl.
*A01H 5/00* (2006.01)

(52) U.S. Cl. ..... Plt./290

(58) Field of Classification Search ..... Plt./290, Plt./287

See application file for complete search history.

*Primary Examiner* — Kent L Bell
(74) *Attorney, Agent, or Firm* — S. Matthew Edwards

(57) ABSTRACT

A new *Chrysanthemum* plant named 'Syndurango Dark' particularly distinguished by the large, dark greyed-orange ray florets, good floriferousness, strong straight stems, and dark foliage.

1 Drawing Sheet

Latin name of the genus and species of the plant claimed: *Chrysanthemum×morifolium.*

Varietal denomination: 'Syndurango Dark'.

BACKGROUND OF THE NEW PLANT

The present invention comprises a new *Chrysanthemum*, botanically known as *Chrysanthemum×morifolium*, and hereinafter referred to by the variety name 'Syndurango Dark'.

'Syndurango Dark' is a product of a planned breeding program. The new cultivar has large, dark greyed-orange ray florets, good floriferousness, strong straight stems, and dark foliage.

'Syndurango Dark' originates as a natural whole plant mutation of 'Yodurango', U.S. Plant Pat. No. 19,736. 'Syndurango Dark' was discovered and selected by the inventor as a single flowering plant within a population of the parent cultivar in a controlled breeding program in Fort Myers, Fla. in February, 2007. The parent cultivar 'Yodurango' has larger foliage, slightly shorter plant habit, ray florets that are a lighter color and wider in width, and is one half to one day faster in flowering response.

The first act of asexual reproduction of 'Syndurango Dark' was accomplished when vegetative cuttings were propagated from the initial selection in May 2007 in a controlled environment in Fort Myers, Fla.

BRIEF SUMMARY OF INVENTION

Horticultural examination of plants grown from cuttings of the plant initiated in May 2007, and continuing thereafter, has demonstrated that the combination of characteristics as herein disclosed for 'Syndurango Dark' are firmly fixed and are retained through successive generations of asexual reproduction.

'Syndurango Dark' has not been observed under all possible environmental conditions. The phenotype may vary significantly with variations in environment such as temperature, light intensity and day length.

A Plant Breeder's Right for this cultivar was applied for in CVPO on Sep. 4, 2009 (#2009-1681). 'Syndurango Dark' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical inflorescence and foliage characteristics of 'Syndurango Dark' with colors being as true as possible with an illustration of this type. The photographic drawing shows four flowering potted plants of the new variety and a close-up of the inflorencenses.

DETAILED BOTANICAL DESCRIPTION

The plant descriptions, measurements and aforementioned photographs were taken in the first week of May 2010 in Gilroy, Calif. under natural light. These plants were started and grown in Nipomo, Calif. and were brought to Gilroy in the first week of May 2010. Plants were grown under conditions which approximate those generally used in commercial potted mum production. These plants used were approximately 10 weeks old.

Color references are made to The Royal Horticultural Society Colour Chart (R.H.S.) 2001.

TABLE 1

DIFFERENCES BETWEEN THE NEW VARIETY 'SYNDURANGO DARK' AND A SIMILAR VARIETY

| | 'Syndurango Dark' | 'Orange Chatham' (U.S. Plant Pat. No. 20,495) |
|---|---|---|
| Flower size/color: | Larger/Darker | Smaller/Lighter |
| Disbudding response: | Suitable | Not suitable |
| Ray floret length: | Longer | Shorter |
| Foliage size: | Larger | Smaller |

Plant:

*Form, growth and habit.*—Herbaceous decorative pot type, stems upright, strong and moderately vigorous growth habit.

*Plant height.*—About 25 cm.

*Plant height* (*inflorescence included*).—36-38 cm.

*Plant width.*—20-23 cm.

Roots:

*Number of days to initiate roots.*—4 days at about 22 degrees C.

*Number of days to produce a rooted cutting.*—10 days at 22 degrees C.

*Type.*—Fine, fibrous, free branching.

*Color.*—RHS N155B but whiter.

Foliage:

*Arrangement.*—Alternate, simple.

*Immature, leaf color, upper surface.*—Darker than RHS 147A.

*Lower surface.*—Closest to RHS 137B.

*Mature, leaf color, upper surface.*—Closest to RHS 147A.

*Lower surface.*—Closest to RHS 137B.

*Length.*—8.5-9.0 cm.

*Width.*—6-7 cm.

*Shape.*—Ovate.

*Base shape.*—Attenuate.

*Apex shape.*—Acute.

*Margin.*—Palmately lobed, serrated.

*Texture, upper surface.*—Bifid T-shape hairs.

*Lower surface.*—Bifid T-shaped hairs.

*Color of veins, upper surface.*—Between RHS 144A and RHS 144B.

*Color of veins, lower surface.*—Closest to RHS 144A.

*Petiole color.*—Closest to RHS 144A.

*Length.*—3.1-3.3 cm.

*Diameter.*—0.3-0.4 cm.

*Texture.*—Bifid T-shaped hairs.

Stem:

*Quantity of main branches per plant.*—4-5.

*Color of stem.*—Closest to RHS 144A but appears lighter because of the hairs.

*Length of stem.*—25-28 cm.

*Diameter.*—0.4-0.6 cm.

*Length of internodes.*—1.5-4.5 cm.

*Texture.*—Heavily covered with Bifid T-shaped hairs.

*Color of peduncle.*—Closest to RHS 144A but appears lighter because of the hairs.

*Length of peduncle.*—4.5-5.5 cm.

*Peduncle diameter.*—0.35 cm.

*Texture.*—Heavily covered with Bifid T-shaped hairs.

Inflorescence:

*Type.*—Composite type, solitary inflorescences (decorative-type) borne terminally above foliage, ray florets arranged acropetally on a capitulum.

*Quantity of short days to flowering* (*response time*).—58-62 days.

*Quantity of inflorescences per plant.*—4-5.

*Lastingness of individual blooms on the plant.*—7-10 days.

*Fragrance.*—Slight.

Bud (just before opening/showing color):

*Color.*—Between RHS 172B and RHS 172C.

*Length.*—2.0-2.75 cm.

*Width.*—2.0 cm.

*Shape.*—Oblate.

Immature inflorescence:

*Diameter.*—9.0 cm.

*Color of ray florets, upper surface.*—RHS N163B ground color, overlaid with RHS N172B to RHS 173B and sometimes with hints of RHS 163B at the apices, margins and basally.

*Lower surface.*—RHS 163C ground color, overlaid with light hues of RHS 169A.

Mature inflorescence:

*Diameter.*—11-13 cm.

*Depth.*—3.0 cm.

*Total diameter of 'disc'.*—0.5-0.6 cm, but is hidden by all the immature ray florets.

*Receptacle height.*—0.6-0.7 cm.

*Receptacle diameter.*—1.2 cm.

Ray florets:

*Average quantity of florets.*—About 175 in numerous whorls.

*Color of florets, upper surface.*—RHS N163B ground color, overlaid with RHS N172B with some hints of RHS 172A mingled in, and hints of RHS 163B at the apices, margins and basally.

*Lower surface.*—RHS 164C ground color, overalaid with RHS 174C.

*Length.*—5.6-6.2 cm.

*Width.*—1.4-1.5 cm.

*Shape.*—Elliptical.

*Apex shape.*—Irregularly emarginate.

*Margin.*—Entire.

*Texture, upper surface.*—Papillose.

*Lower surface.*—Papillose.

Disc florets:

*Average quantity of florets.*—About 40.

*Color of florets.*—RHS 1D with RHS 144B apex and RHS 155D basally.

*Length.*—0.5 cm.

*Width.*—0.1 cm.

*Shape.*—Tubular, enlongated.

*Apex shape.*—Acute, 5 pointed.

Phyllaries:

*Quantity.*—About 25.

*Color, upper surface.*—RHS 147A.

*Lower surface.*—RHS 147A but appears very grey because of all the hairs.

*Length.*—1.1-1.3 cm.

*Width.*—0.3-0.35 cm.

*Shape.*—Ligulate.

*Apex shape.*—Acute.

*Based.*—Fused.

*Margins.*—Entire; papery.

*Texture, upper surface.*—Glabrous, smooth.

*Lower surface.*—Bifid T-shaped hairs.

Reproductive organs:

*Pistil.*—1, found all both types of florets.

*Length.*—0.6 cm.

*Style color.*—RHS 1B but lighter.

*Style length.*—0.5 cm.

*Stigma color.*—RHS 144A.

*Stigma shape.*—Bi-parted.

*Ovary color.*—Not observed.

*Stamens.*—1, found only on the disc florets.

*Color of filaments.*—RHS 1B but less intense.

*Length filaments.*—0.3-0.4 cm.

*Anther color.*—RHS 13A.

*Anther length.*—0.2 cm.

*Anther shape.*—Oval to oblong.

*Color of pollen.*—Not observed.

*Pollen amount.*—Not observed.

*Fertility/seed set.*—Has not been observed on this hybrid.

Disease/pest resistance: Disease/pest resistance has not been observed on this hybrid.

What is claimed is:

1. A new and distinct variety of *Chrysanthemum* plant named 'Syndurango Dark' substantially as illustrated and described herein.

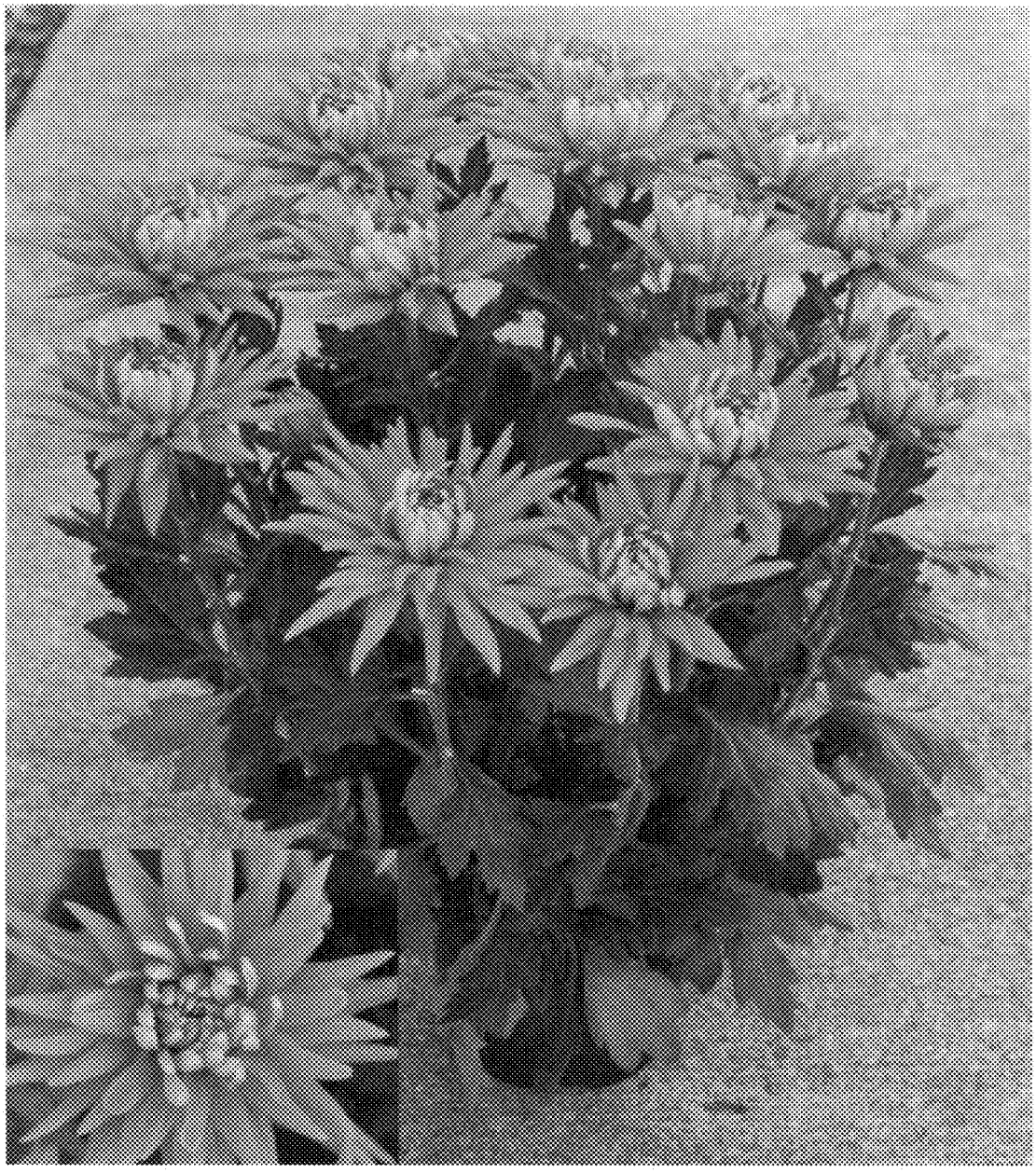

* * * * *